(12) United States Patent
King

(10) Patent No.: US 9,274,076 B2
(45) Date of Patent: Mar. 1, 2016

(54) LOW SLOPE PH ELECTRODE WITH CHARGE TRANSFER COMPONENT

(71) Applicant: Hach Company, Loveland, CO (US)

(72) Inventor: Karl Lewis King, Windsor, CO (US)

(73) Assignee: Hach Company, Loveland, CO (US)

( * ) Notice: Subject to any disclaimer, the term of this patent is extended or adjusted under 35 U.S.C. 154(b) by 0 days.

(21) Appl. No.: 13/832,685

(22) Filed: Mar. 15, 2013

(65) Prior Publication Data
US 2014/0262779 A1    Sep. 18, 2014

(51) Int. Cl.
*G01N 27/30* (2006.01)
*G01N 27/36* (2006.01)
*G01N 27/333* (2006.01)

(52) U.S. Cl.
CPC .............. *G01N 27/302* (2013.01); *G01N 27/36* (2013.01); *G01N 27/333* (2013.01); *Y10T 29/49117* (2015.01)

(58) Field of Classification Search
CPC .................................................. G01N 27/4161
USPC ........ 204/412, 416, 433, 435; 205/787.5, 789
See application file for complete search history.

(56) References Cited

U.S. PATENT DOCUMENTS

| | | | | |
|---|---|---|---|---|
| 3,959,107 A | * | 5/1976 | Horner et al. | 204/415 |
| 4,650,562 A | * | 3/1987 | Harman et al. | 204/420 |
| 4,822,456 A | * | 4/1989 | Bryan | G01N 27/4165 |
| | | | | 204/412 |
| 2009/0032397 A1 | * | 2/2009 | Woodward et al. | 204/416 |
| 2009/0101524 A1 | * | 4/2009 | Woodward et al. | 205/787.5 |
| 2010/0224490 A1 | * | 9/2010 | King et al. | 204/412 |

FOREIGN PATENT DOCUMENTS

EP    2293052 A1    3/2011
WO    2007109521 A1    9/2007

OTHER PUBLICATIONS

"The Superiority of the Differential pH Electrode System", Technical Bulletin TB-P5, Dec. 31, 2005, 4 pages, Hach Company. Available at http://www.hach.com/cms-portals/hach_com/cms/documents/pdf/TechInfo-Bulletins-Specs/TheSuperiorityoftheDifferentialpHElectrodeSystem.pdf. Last accessed Sep. 24, 2014.
International Search Report for Application PCT/US2014/024474, Jun. 16, 2014, 4 pages, European Patent Office, The Hague, Netherlands.

* cited by examiner

*Primary Examiner* — Luan Van
*Assistant Examiner* — Steven Rosenwald
(74) *Attorney, Agent, or Firm* — Ference & Associates LLC

(57) ABSTRACT

An aspect includes a low slope electrode device, including: at least one electrode; at least one container at least partially enclosing the at least one electrode and having at least one ion sensitive region; an external buffer container having at least one separating element that separates said at least one ion sensitive region into: a first ion sensitive area separating an internal buffer solution bathing the at least one electrode and an external sample solution; and a second ion sensitive area separating the internal buffer solution bathing the at least one electrode and an external buffer solution; wherein the at least one separating element, the first ion sensitive area, and the second ion sensitive area establish a charge flow circuit. Other aspects are described and claimed.

13 Claims, 5 Drawing Sheets ered to use readings of relative voltage, as sensed through measuring and reference electrodes, to calculate an ion concentration (hydrogen ion concentration in the case of pH metering). Typically, a voltage is sensed by an electrode measuring half cell and a voltage is sensed by a reference half cell that are electrically connected to a suitable measuring meter (meter circuitry). It is well known that hydrogen ion concentration in a given sample solution can be measured with such a pH measuring system.

LOW SLOPE PH ELECTRODE WITH CHARGE TRANSFER COMPONENT

BACKGROUND

The subject matter described herein relates generally to devices and methods for the measurement of a specific ion activity or concentration in solution based on potentiometric sensors (potential difference or voltage based measuring). An example of such measuring is use of a pH meter to determine the pH of a solution.

In a potentiometric measuring system, meter circuitry is designed to use readings of relative voltage, as sensed through measuring and reference electrodes, to calculate an ion concentration (hydrogen ion concentration in the case of pH metering). Typically, a voltage is sensed by an electrode measuring half cell and a voltage is sensed by a reference half cell that are electrically connected to a suitable measuring meter (meter circuitry). It is well known that hydrogen ion concentration in a given sample solution can be measured with such a pH measuring system.

In a conventional set up, reference electrodes (for example Ag/AgCl electrodes) are used together with measuring electrodes in a complete cell. These reference electrodes and measuring electrodes may be used in concert to determine ion concentration in a sample (for example, pH or another ion). The reference electrode is designed in order to maintain its potential as constant as possible throughout the measuring process. In contrast, the measuring electrode is designed such that its potential is a function of the concentration of the ion being tested. Constancy of the reference electrode's potential has been achieved by the presence of a saturated electrolyte salt bridge or junction. The reference electrolyte leaks slowly through the junction. The relative potential difference between the reference and measuring electrodes may be used to calculate the concentration of the ion in the sample, and may be displayed on a millivolt (mV) instrument (potentiometer).

The potential of a complete cell may be represented by:

$$E_{Cell} = E_{meas} - (E_{ref} + E_j)$$

where $E_{meas}$, $E_{ref}$, and $E_j$ are the potentials of the measuring electrode, the reference electrode and the junction.

The electrode half cells (reference and measuring) are electrically connected to a pH meter circuitry to produce measurements in millivolts. The millivolt readings can be used to represent hydrogen ion activity in the solution being measured. Such conventional systems and the parts thereof are well known to those skilled in the art and are available in the commercial marketplace from various manufacturers such as Hach Company of Loveland, Colo. Thus, when the description set forth herein references examples referring to conventional components such as pH glass, it is intended to mean a conventional component such as pH glass of the type which is sold in the commercial marketplace by Hach Company of Loveland, Colo.

BRIEF SUMMARY

In summary, one aspect provides a low slope electrode device, comprising: at least one electrode; at least one container at least partially enclosing the at least one electrode and having at least one ion sensitive region; an external buffer container having at least one separating element that separates said at least one ion sensitive region into: a first ion sensitive area separating an internal buffer solution bathing the at least one electrode and an external sample solution; and a second ion sensitive area separating the internal buffer solution bathing the at least one electrode and an external buffer solution; wherein the at least one separating element, the first ion sensitive area, and the second ion sensitive area establish a charge flow circuit.

Another aspect provides a system, comprising: at least one low slope electrode device, comprising: at least one electrode; at least one container at least partially enclosing the at least one electrode and having at least one ion sensitive region; an external buffer container having at least one separating element that separates said at least one ion sensitive region into: a first ion sensitive area separating an internal buffer solution bathing the at least one electrode and an external sample solution; and a second ion sensitive area separating the internal buffer solution bathing the at least one electrode and an external buffer solution; wherein the at least one separating element, the first ion sensitive area, and the second ion sensitive area establish a charge flow circuit; at least one measuring electrode device; and a processor configured to utilize signals derived from the at least one low slope electrode device and the at least one measuring electrode device to produce a pH measurement output.

A further aspect provides a method, comprising: forming at least one low slope electrode device comprising at least one electrode, at least one container at least partially enclosing the at least one electrode and having at least one ion sensitive region, an external buffer container having at least one separating element that separates said at least one ion sensitive region into: a first ion sensitive area separating an internal buffer solution bathing the at least one electrode and an external sample solution, and a second ion sensitive area separating the internal buffer solution bathing the at least one electrode and an external buffer solution, wherein the at least one separating element, the first ion sensitive area, and the second ion sensitive area establish a charge flow circuit; forming at least one measurement electrode device comprising at least one measurement electrode; and connecting the at least one low slope electrode device and the at least one measurement electrode device to meter circuitry, the meter circuitry comprising a processor configured to utilize signals derived from the at least one low slope electrode device and the at least one measuring electrode device to produce a pH measurement output.

The foregoing is a summary and thus may contain simplifications, generalizations, and omissions of detail; consequently, those skilled in the art will appreciate that the summary is illustrative only and is not intended to be in any way limiting.

For a better understanding of the embodiments, together with other and further features and advantages thereof, reference is made to the following description, taken in conjunction with the accompanying drawings. The scope of the invention will be pointed out in the appended claims.

DETAILED DESCRIPTION

Figure 1:
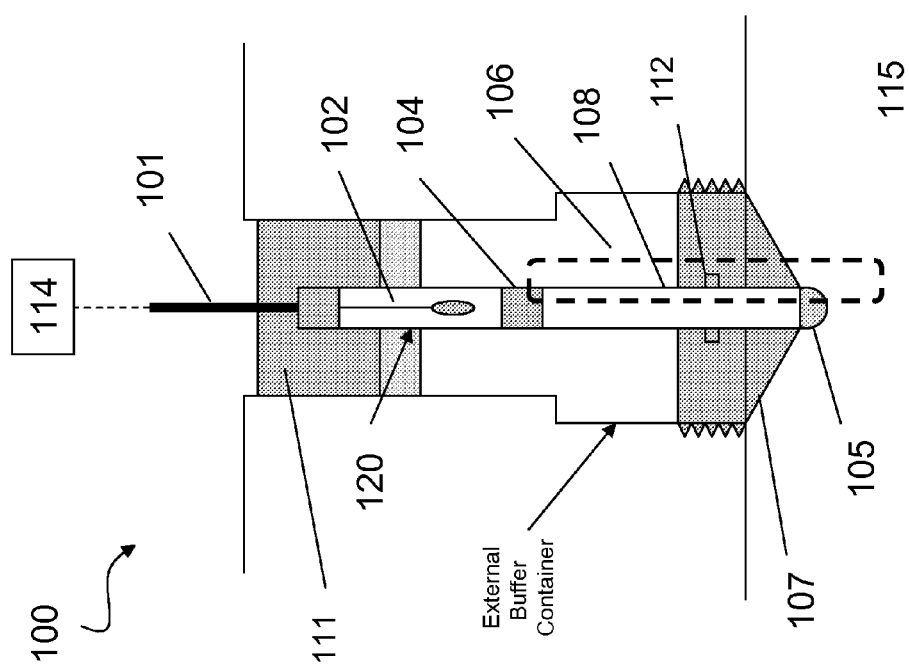
FIG. 1 illustrates a cross sectional view of an example low slope electrode device.

It will be readily understood that the components of the embodiments, as generally described and illustrated in the figures herein, may be arranged and designed in a wide variety of different configurations in addition to the described example embodiments. Thus, the following more detailed description of the example embodiments, as represented in the figures, is not intended to limit the scope of the embodiments, as claimed, but is merely representative of example embodiments.

Reference throughout this specification to "one embodiment" or "an embodiment" (or the like) means that a particular feature, structure, or characteristic described in connection with the embodiment is included in at least one embodiment. Thus, appearances of the phrases "in one embodiment" or "in an embodiment" or the like in various places throughout this specification are not necessarily all referring to the same embodiment.

Furthermore, the described features, structures, or characteristics may be combined in any suitable manner in one or more embodiments. In the following description, numerous specific details are provided to give a thorough understanding of example embodiments. One skilled in the relevant art will recognize, however, that various embodiments can be practiced without one or more of the specific details, or with other methods, components, materials, et cetera. In other instances, well-known structures, materials, or operations are not shown or described in detail. The following description is intended only by way of example, and simply illustrates certain example embodiments.

In conventional potentiometric measuring systems, reference electrodes have many problems and it is desirable to remove, eliminate or otherwise re-design conventional type reference electrodes in potentiometric systems. One attempt included treating pH sensitive glass to desensitize it, thus permitting use of the electrode as a reference electrode even if placed into the external sample solution. Unfortunately, this and other attempts have proven impractical.

Embodiments provide a low slope electrode by forming electrical impedances in series such that a voltage divider is formed. Thus, the low slope electrode device has reduced voltage sensitivity in terms of measured voltage between an internal buffer solution and an external (sample) solution. Hence, a low slope electrode is produced and may be used in potentiometric metering systems, such as a pH meter.

Low slope electrodes, as described in connection with the example embodiments illustrated in the figures, when used in conjunction with other measuring electrodes, permits determining relative voltage potential, and thus calculation of ion activity such as represented in a pH value. By using measuring electrodes having different internal pH solutions, electrode degradation over time may be compensated. For example, using a measuring electrode with an internal solution of pH 7, another measuring electrode solution of pH 4, along with one or more other electrodes, as further described herein, permits compensating for electrode degradation over time by comparison of measuring electrode slopes, which are independent of sample pH.

Figure 5:
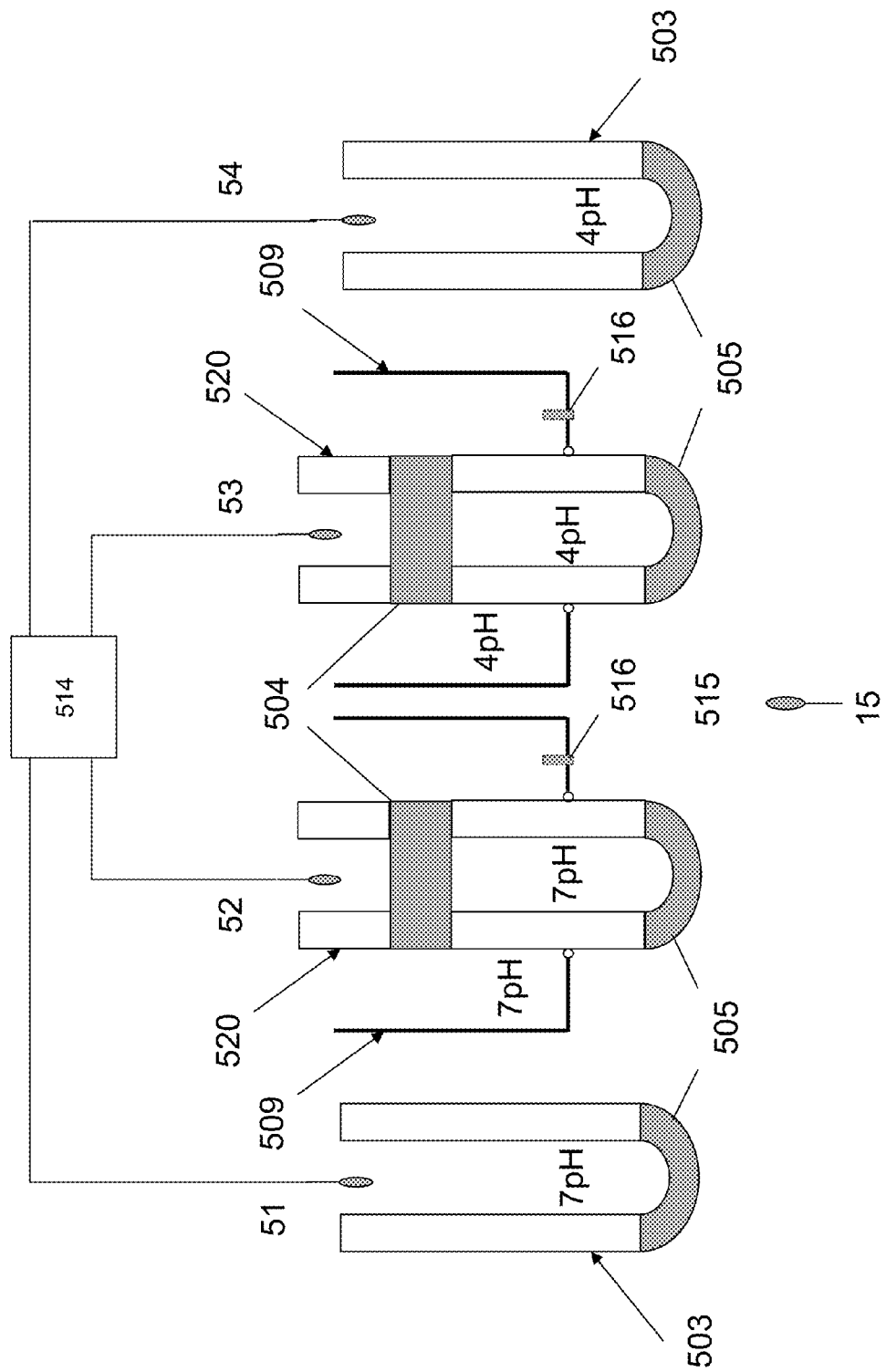
FIG. 5 illustrates a cross sectional view of an example pH metering system having low slope electrode devices.

An example of the calculation of a pH value from four electrode signals (for example, as provided by a device such as illustrated in FIG. 5) is given. Those skilled in the state of the art will observe that the equations shown give a basic method without every detail of computation.

pH Measurement Example

High slope electrodes (e.g., standard sensitivity pH electrodes) and low slope electrodes (e.g., reduced sensitivity pH electrodes, as described herein) may be used in pairs (e.g., two pairs of high and low slope electrodes with differing fill buffers, as illustrated in FIG. 5) for measurement. The electrode pairs may also provide for drift compensation (e.g., as often encountered with aging pH probes). In terms of symbols used in this example, U1 is the potential difference between the pair of electrodes with high pH buffer fill (e.g., pH 7). U2 is the potential difference between the pair of electrodes with low pH buffer fill (e.g., pH 4). S1 is the difference of the two slopes, high and low, in the U1 pair found at time of system calibration. S2 is the difference of the two slopes, high and low, in the U2 pair found at time of system calibration. pHH is the pH of the high pH internal fill buffer. pHL is the pH of the low pH internal fill buffer. pHx is the pH of the external sample solution (e.g., 115 of FIG. 5) the two electrode pairs measure.

Equations of Operation

The potentials U1 and U2 are given by:

$$U1 = S1 \cdot (pHH - pHx); \text{ and}$$

$$U2 = S2 \cdot (pHH - pHx).$$

These can be solved for pH in the well known way. pHx may be found using:

$$pHx = pHH - U1/S1; \text{ and}$$

$$pHx = pHL - U2/S2.$$

If the slopes S1 and S2 drift over time, e.g., S1→S1+dS1, and S2→S2+dS2, the pHx values calculated from the equations above will be in error. If the drift of the two pairs is proportional, however, an accurate pH can nevertheless be calculated.

In the drifted state, $$U1 = (S1 + dS1) \cdot (pHH - pHx); \text{ and}$$

$$U2 = (S2 + dS2) \cdot (pHL - pHx).$$

If the drift follows the assumption of proportionality, i.e., (S1+dS1)/(S2+dS2)=S1/S2, then solving the above three equations gives:

$$pHx = (U1 \cdot pHL/S1 - U2 \cdot pHH/S2)/(U1/S1 - U2/S2),$$

where S1 and S2 are the slope values obtained at time of calibration. In the following description of example embodiments, various arrangements are provided for establishing a low slope electrode for use in pH probes.

EXAMPLE 1

In FIG. 1 is illustrated an example low slope electrode device 100. The example low slope electrode device 100 includes a lead wire 114 to an Ag:AgCl electrode 101 bathed in an internal buffer solution 102 enclosed at the top, e.g., via epoxy region 111, in turn contained in a glass container 120. The glass container 120 contains different elements, areas or regions. Glass container 120 contains pH glass elements 104, 105, separated by insulating glass 108, that provide a voltage interface for the internal buffer solution 102 with the external buffer solution 106 and the external sample solution 115, respectively. The pH glass elements 104, 105 each permit charge flow with a resistance/impedance, as does charge transfer component 107.

Thus, by inclusion of a separating element (in this example, the charge transfer component 107 with an o-ring 112) a charge path is established (illustrated by dashed line in the figures) whereby charge moves in a path between the internal buffer solution 102, the external buffer solution 106, and the external sample solution 115. Electrical impedances provided by the pH glass elements 104, 105, while not absolute, is/are substantial relative to the essentially unimpeded electric path provided by the buffer and sample solutions. Thus, resistors are provided in series at least by the pH glass elements 104 and 105 in the charge path. This forms a voltage divider to create a low voltage ($V_{out}$, measured by the Ag:AgC electrode 101) relative to the voltage between the external sample solution 115 and the internal buffer solution 102, forming an electrode having a "low slope" in comparison with a conventional measuring glass electrode (conventional pH electrodes have a sensitivity of about 59 mV/pH unit). In a number of embodiments a low slope electrode has sensitivity of less than the normal pH glass electrode which is 59 mV/pH unit. In a number of embodiments hereof, such a low slope electrode has a sensitivity of about ¾, ⅔, ½ or even lower than the "normal" pH glass electrodes. The sensitivity may be modified as desired by providing different electric impedances.

EXAMPLE 2

FIG. 2A illustrates the example of FIG. 1 in a slightly different format. Nonetheless, the pH glass elements 204, 205 of container 220, separated by insulating glass 208, and charge junction 216 form a path for charge flow with in-series impedances provided by the pH glass elements 204, 205, as illustrated and described in connection with FIG. 1, allowing for reduced voltage, as sensed between measuring electrodes 10 (VA) and 11 (VB) and 12 (VD) (measuring potential difference between internal buffers 202, 206 and external sample solution 215).

Figure 2:
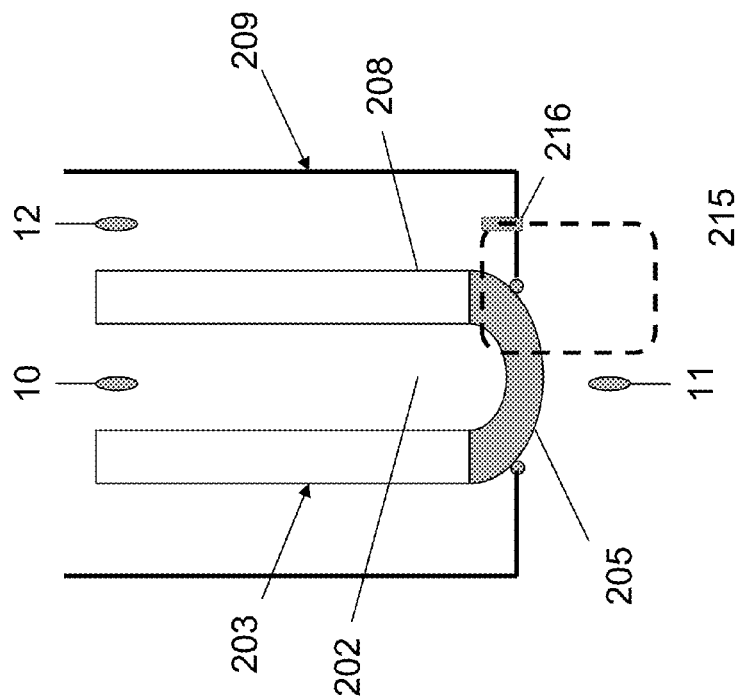
FIG. 2(A-B) illustrates a cross sectional view of example low slope electrode devices.
Figure 2:
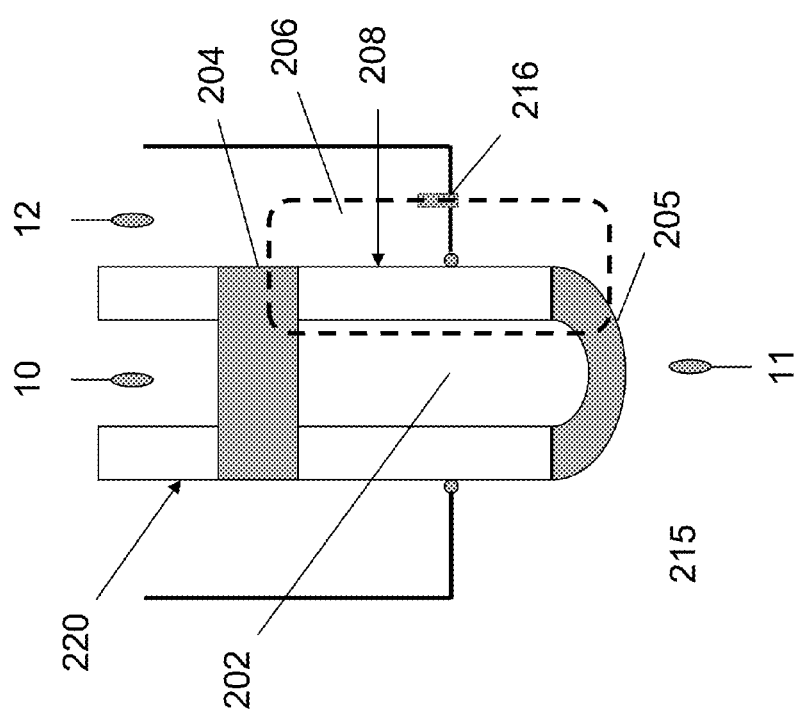

In contrast, in FIG. 2B, a container 203 provides a pH glass element 205 and an insulating glass 208 provides both impedances, again in series, in connection with a separating element (the external buffer container 209). The insulating glass 208 prevents charge flow (essentially an infinite impedance to charge flow), while the external buffer container 209 acts as a separating element and divides the single pH glass element 205 into two functional impedances in the charge flow path (again indicated by the dashed line). In FIG. 2(A-B), the potential VA-VD (measured by measuring electrodes 10, 12 and 11, respectively) provides a potential for the low slope electrode.

EXAMPLE 3

Figure 3:
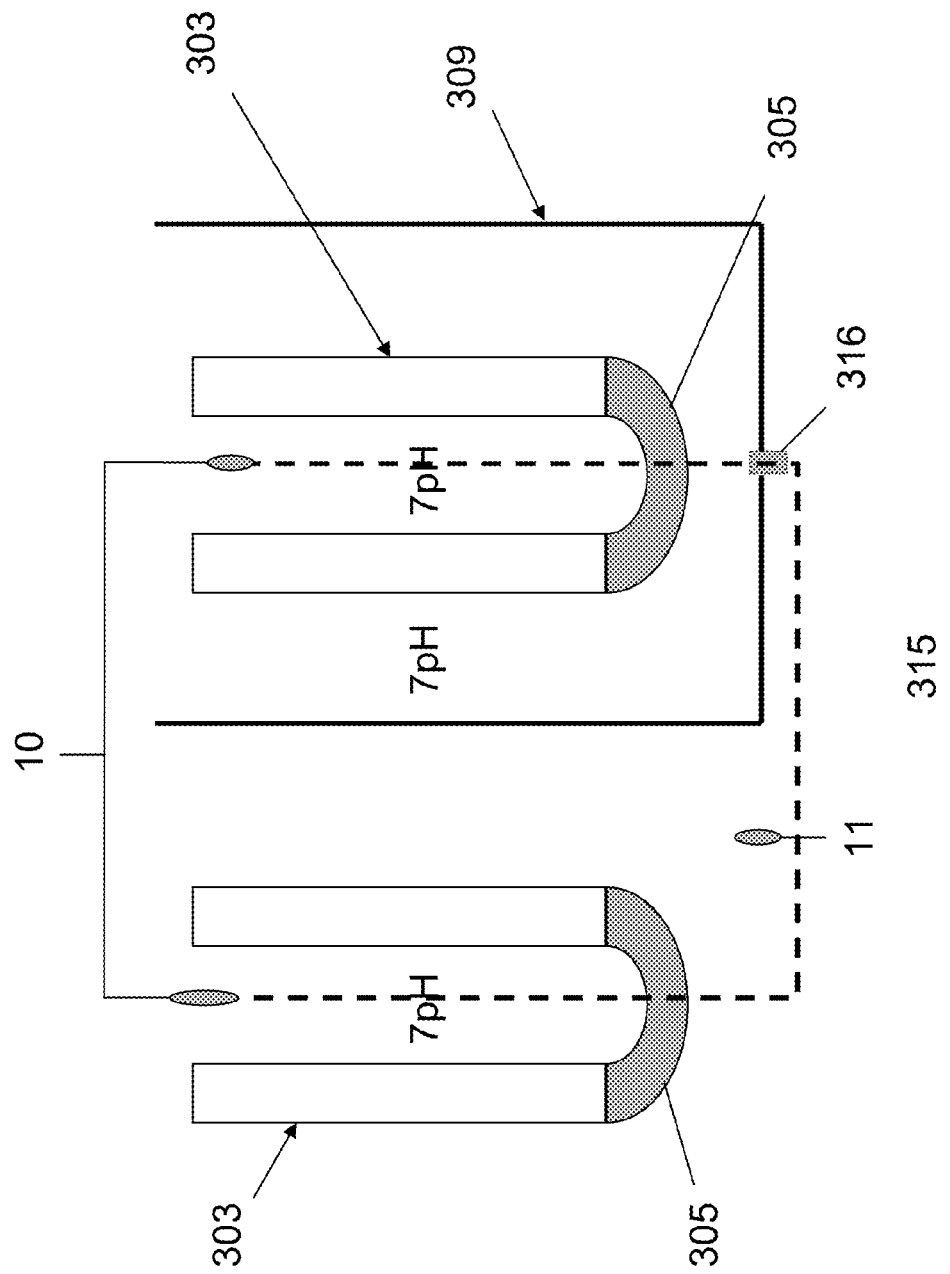
FIG. 3 illustrates a cross sectional view of an example low slope electrode device.

More than one piece or component may be used to form the impedances in a serial arrangement. For example, as illustrated in FIG. 3, a first container (or container element) 303 provides a pH glass element 305 interface and electrical impedance between buffer (pHB, e.g., pH 7) and the external sample solution 315. A second container 303, which may be identical to the first container element, includes a second pH glass element 305 and electrical impedance between internal buffer pHB (e.g., pH 7) and external buffer pHB (e.g., pH 7, with the external buffer pHB being contained by the external buffer container 309 that also serves as a separating element), which is in turn connected to the external sample solution 315 via a junction 316. Charge follows a path along the dashed line and an electrode measuring VA (as sensed by measuring electrode 10) registers reduced voltage due to pH glass elements 305 forming electrical impedances in series (forming a voltage divider arrangement). As with Examples 1 and 2, the example two-piece low slope electrode device illustrated in FIG. 3 may be used in conjunction with a measuring electrode in order to measure pH of an external sample solution 315. In FIG. 3, the potential VA-VB (as sensed by measuring electrode 10, 11) provides a potential for the low slope electrode.

EXAMPLE 4

Figure 4:
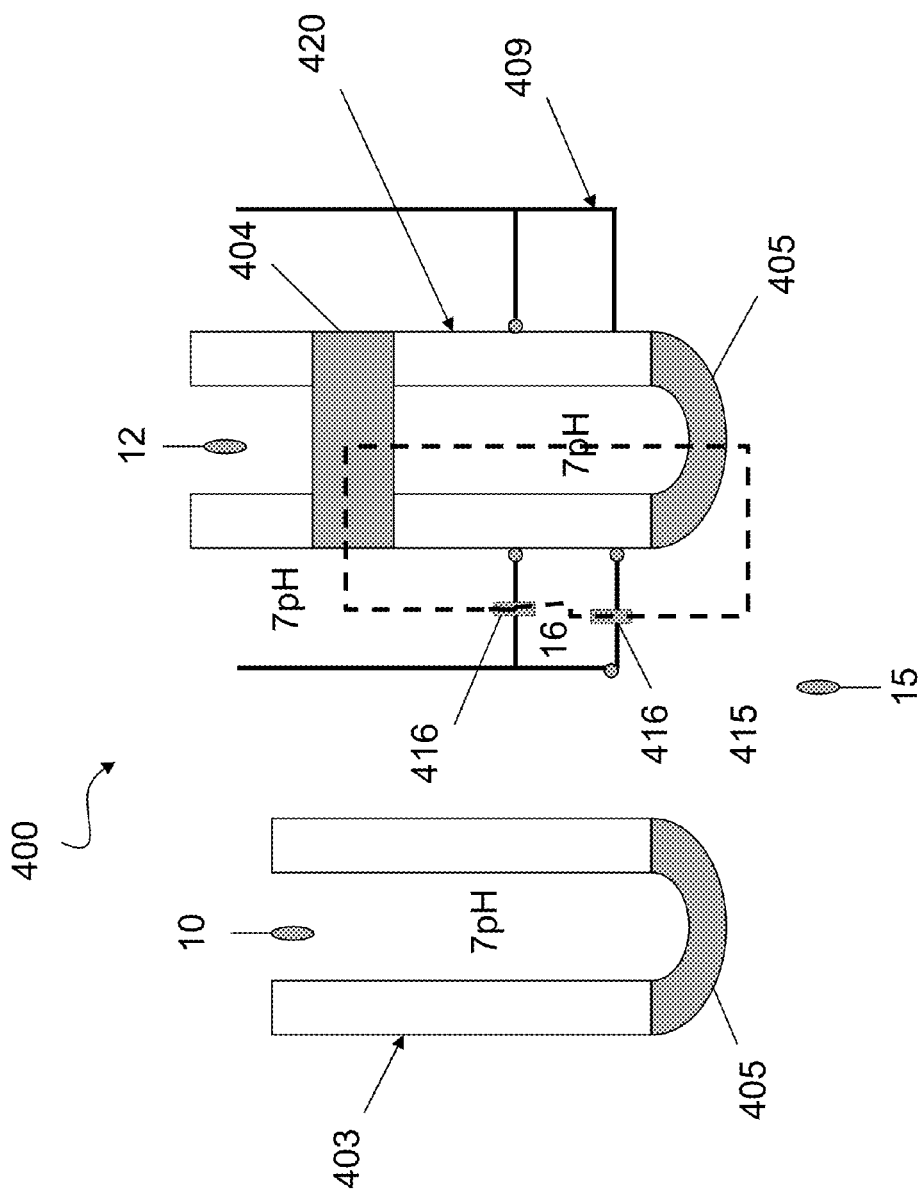
FIG. 4 illustrates a cross sectional view of an example pH measuring device having a low slope electrode device.

As illustrated in FIG. 4, many arrangements are conceivable for forming a pH measuring device having low slope electrode(s) using impedances in a serial arrangement. For example, a low slop electrode is illustrated in FIG. 4 paired with a measuring electrode. A container 403 forming a measuring electrode provides a pH glass elements 405 interface between buffer internal thereto (e.g., pHB 7) and the external sample solution 415, which registers a voltage (as sensed by measuring electrode 10). A multi-component low slope electrode includes electrical impedances in series via provisioning pH glass elements 404, 405 on container 420. Additionally, a external buffer container 409 (and junctions 416 thereof) sets up a circuit loop, wherein charge flow between buffer solutions of container 420 (e.g., pHB 7 and salt bridge solution (SB) 16) and external sample solution 415 is provided. The circuit loop is indicated by the dashed line in FIG. 4. Charge follows a path along the dashed line and the measuring electrode 12 registers reduced voltage (in comparison with measuring electrode 10) due to pH glass elements 404 and 405 forming electrical impedances in series (forming a voltage divider arrangement).

As with Examples 1, 2 and 3, the example low slope electrode device 400 illustrated in FIG. 4 may be used in conjunction with a measuring electrode, formed by container 403 in FIG. 4, in order to measure pH of external sample solution 415. Appropriate buffering chamber(s) and solutions may be employed to prevent adverse reaction between the salt bridge solution 16 and the process (external sample solution 415). An example salt bridge solution 16 may include 1M KCl. In FIG. 4, the potential (VA–VD) difference between measuring electrodes 10, 12 and ground electrode 15 provides a potential for the measurement of the pH of the external sample solution 415.

EXAMPLE 5

As an example of a potentiometric measuring system including low slope electrodes as described herein, a four electrode arrangement may be employed to utilize the low slope electrodes (formed by containers 520) along with two measuring electrodes (formed by containers 503) to compensate for electrode degradation over time. For example, in FIG. 5, one measuring electrode and one low slope electrode may be paired, e.g., may each contain an internal buffer of a certain pH, for example 7. Similarly, another low slope electrode and another measuring electrode may be paired, e.g., may each contain an internal buffer of a different pH, for example 4.

In FIG. 5, the low slope electrodes are formed of a container 520 including two pH glass elements 504, 505, enclosed using an external buffer container 509 and connected to the external sample solution 515 via a junction element 516. A charge flow circuit is thereby established between internal buffers (e.g., pH 7) and the external sample solution 515. Another low slope electrode is similarly formed but having different internal buffer solutions (e.g., pH 4). Measuring electrodes are appropriately paired with each low slope electrode (i.e., having matching internal/fill buffers, pH 4 and pH 7 as illustrated in FIG. 5).

As is known, a four electrode arrangement may provide signals to a meter 514 (e.g., via AgCl electrode lines 51, 52, 53, 54) utilizing differing pH buffers to compensate/correct for changes (degradation) of electrodes over time. Thus, low slope electrodes commensurate with embodiments described herein (provided via containers 520 and related components in this example) may be utilized in such a four electrode arrangement, along with a ground electrode 15 (for example, a piece of metal) in lieu of standard reference electrode(s). In FIG. 5, the potential provided by the AgCl electrode lines 51, 52 and 53, 54 provide comparable potentials for the measurement of the pH of the external sample solution 515 and for calibration over time.

Embodiments, as described in connection with the non-limiting examples above, provide a low slope electrode device by forming electrical impedances in series such that a voltage divider is formed. Thus, the low slope electrode device has reduced voltage sensitivity in terms of measured voltage between an internal buffer solution and an external (sample) solution and may be exposed to the external sample solution. While not specifically illustrated, measurement of temperature of the external sample may be added by use of a standard component and used in ion concentration calculations. Hence, embodiments provide a low slope electrode device that may be used in potentiometric metering systems, such as a pH meter.

For example, in FIG. 5, a potentiometric measuring system for measuring pH is illustrated, including electrode measuring assemblies and low slope electrode assemblies. Each of the measuring and low slope electrode assemblies, as described herein, contain at least one pH glass element 505. As described, the low slope electrode devices contain voltage divider arrangements, which may be formed using a container 520 having two pH glass elements 504, 505. Each of the measuring and low slope electrode assemblies may be connected (e.g., AgCl electrode lines 51, 52, 53, and 54) to an amplifier (not shown) that acts to amplify the electrical signals transmitted from the respective assemblies to the meter 514.

Generally, the signals are ultimately communicated to a potentiometric meter circuitry, which includes components for measuring and extrapolating millivolt changes of the external sample solution in order to provide a pH calculation. The meter circuitry may comprise a processor configured to utilize signals derived from at least one low slope electrode device and at least one measuring electrode device to produce a pH measurement output. This system differs from the conventional systems in that reference electrode half cells are omitted in favor of inclusion of the low slope electrode assemblies and a metal/ground rod. The operation of the example system illustrated in FIG. 5 is commensurate with the conventional and well known systems presently in use (but having reference electrode half cells) and therefore those skilled in the art will readily understand how the illustrated example system of FIG. 5 operates.

In the example system of FIG. 5 the measuring electrodes and the low slope electrodes, which may be considered measuring electrodes as well, albeit with lowered ion sensitivity, may be calibrated with suitable buffer solutions (for example, of pH 4 and 7) and a variable span analyzer in accordance with methods already known for calibrating such measuring cells before the system is put into actual use in a external sample solution. In use, as the potentials sensed by the measuring electrodes and the low slope electrodes change, these can be compared against one another to provide a pH measurement which is equivalent to the hydrogen ion activity in the external sample solution being monitored. The sensed potentials can be extrapolated by the potentiometric meter circuitry to provide the hydrogen ion concentration in the external sample solution by conventional means.

The various embodiments may be combined in a variety of ways. For example, in considering the example of a low slope electrodes illustrated in FIG. 5, i.e., arrangements using containers 520, it should be noted that one may substitute the low slope electrode arrangement of FIG. 3 therefor. Thus, the low slope electrode of FIG. 3 (formed of two containers 303) may take the place of container 520 (formed of one piece of having two pH glass elements 504, 505), and likewise another low slop electrode of FIG. 3 (formed of two containers 303) may take the place of the other low slope electrode (formed of an additional container 520 having two pH glass elements 504, 505) in FIG. 5. The result is a six glass piece pH probe, with two low slope electrodes (of the form of FIG. 3) having four pieces in total, along with two high slope/normal sensitivity electrodes.

An advantage of such a six piece arrangement includes reduced cost of components, and reduced cost of the probe overall, even though more physical components are utilized. This result flows from the low cost of glass (and other components) used to form an arrangement such as in FIG. 3 as compared to the cost of the glass used to form a low slope electrode of form illustrated in FIG. 5. The low slope arrangement of FIG. 3 is lower cost by virtue of utilizing a container 303 having only one pH glass element 305 versus a container 520 having two pH glass elements thereon (504, 505). Thus, a six piece arrangement, as described herein as a modification of FIG. 5 with low slope electrodes of FIG. 3, results in a lower cost pH probe having six identical containers of the form of container 303/503 (illustrated in FIG. 3 and FIG. 5, respectively).

This disclosure has been presented for purposes of illustration and description but is not intended to be exhaustive or limiting. Many modifications and variations will be apparent to those of ordinary skill in the art. The embodiments were chosen and described in order to explain principles and practical application, and to enable others of ordinary skill in the art to understand the disclosure for various embodiments with various modifications as are suited to the particular use contemplated.

Although illustrative embodiments have been described herein, it is to be understood that the embodiments are not limited to those precise embodiments, and that various other changes and modifications may be affected therein by one skilled in the art without departing from the scope or spirit of the disclosure.

What is claimed is:

1. A low slope electrode device, comprising:
   a first measuring electrode in an external sample solution;
   a second measuring electrode in an external buffer solution;
   a third measuring electrode operatively coupled to the first measuring electrode and the second measuring electrode;
   a glass container including an internal buffer solution and at least partially enclosing the third measuring electrode, the glass container having two pH sensitive regions separated by insulating glass;
   an external buffer container including the external buffer solution; and
   a separating element that separates the internal buffer solution and the external sample solution;
   wherein:
   a first pH sensitive region of the glass container permits charge flow between the internal buffer solution and the external sample solution;

a second pH sensitive region of the glass container permits charge flow between the internal buffer solution and the external buffer solution; and the separating element, the first pH sensitive region, and the second pH sensitive region establish a charge flow circuit through the internal buffer solution, the external buffer solution, and the external sample solution; and the charge flow circuit acts as a voltage divider for the measuring electrode of the low slope electrode device.

2. The low slope electrode device of claim 1, wherein the first pH sensitive region and the second pH sensitive region are formed of pH glass.

3. The low slope electrode device of claim 1, wherein the glass container is a single container; and wherein the first pH sensitive region and the second pH sensitive region are disposed on the single container and separated via insulating glass.

4. The low slope electrode device of claim 3, wherein the separating element contacts the insulating glass separating the first pH, sensitive region and the second pH sensitive region and defines a chamber containing the external buffer solution.

5. The low slope electrode device of claim 1, wherein the separating element comprises a junction element separating the external buffer solution from the external sample solution.

6. A system, comprising:
at least one low slope electrode device, comprising:
a first measuring electrode in a sample solution;
a second measuring electrode in an external buffer solution;
a third measuring electrode operatively coupled to the first measuring electrode and the second measuring electrode;
a glass container including an internal buffer solution and at least partially enclosing the third measuring electrode, the glass container having two pH sensitive regions separated by insulating glass; and
an external buffer container including the external buffer solution; and
a separating element that separates the internal buffer solution and the external sample solution;
wherein:
a first pH sensitive region of the glass container permits charge flow between the internal buffer solution and the external sample solution;
a second pH sensitive region of the glass container permits charge flow between the internal buffer solution and the external buffer solution; and
the separating element, the first pH sensitive region, and the second pH sensitive region establish a charge flow circuit through the internal buffer solution, the external buffer solution, and the external sample solution; and
the charge flow circuit acts as a voltage divider for the measuring electrode of the low slope electrode device;
at least one non-low slope measuring electrode device;
the system further comprising a processor configured to utilize signals derived from the at least one low slope electrode device and the at least one non-low slope measuring electrode device to produce a pH measurement output.

7. The system of claim 6, wherein:
the at least one low slope electrode device comprises at least two low slope electrode devices; and
the at least one non-low slope measuring electrode device comprises at least two non-low slope measuring electrode devices.

8. The system of claim 7, wherein:
a first of the at least two low slope electrode devices comprises an internal buffer solution of about pH 4;
a second of the at least two low slope electrode devices comprises an internal buffer solution of about pH 7;
a first of the at least two non-low slope measuring electrode devices comprises an internal buffer solution of about pH 4; and
a second of the at least two non-low slope measuring electrode devices comprises an internal buffer solution of about pH 7.

9. The system of claim 8, wherein:
the first of the at least two low slope electrode devices and the first of the at least two non-low slope measuring electrode devices comprise a first electrode pair; and
the second of the at least two low slope electrode devices and the second of the at least two non-low slope measuring electrode devices comprise a second electrode pair.

10. A low slope electrode device, comprising:
a first measuring electrode in an external sample solution;
a second measuring electrode in an external buffer solution;
a third measuring electrode operatively coupled to the first measuring electrode and the second measuring electrode;
at least one container at least partially enclosing the third measuring electrode and having at least one pH sensitive region;
an external buffer container having at least one separating element that separates said at least one pH sensitive region into:
a first pH sensitive area separating an internal buffer solution bathing the third measuring electrode and the external sample solution; and
a second pH sensitive area separating the internal buffer solution bathing the third measuring electrode and the external buffer solution;
wherein:
the at least one separating element, the first pH sensitive area, and the second pH sensitive area establish a charge flow circuit; and
the charge flow circuit acts as a voltage divider for the measuring electrode of the low slope electrode device.

11. The low slope electrode device of claim 10, wherein the at least one container element is a single container;
wherein the at least one pH sensitive region is a single pH sensitive region; and
wherein the single pH sensitive region of the single container is separated by the at least one separating element to form the first pH, sensitive area and the second pH sensitive area.

12. The low slope electrode device of claim 10, wherein the at least one container comprises two containers;
wherein a first of the two containers contains the first pH sensitive region;
wherein a second of the two containers contains the second pH sensitive region; and
wherein the at least one separating element defines a chamber containing the external buffer solution.

13. The low slope electrode device of claim 12, wherein the first of the two containers comprises the measuring electrode electrically connected to the second of the two containers.

* * * * *